US012778855B2

(12) United States Patent
Thelin et al.

(10) Patent No.: US 12,778,855 B2
(45) Date of Patent: Nov. 3, 2026

(54) PACIFIER

(71) Applicant: URSATEC GmbH, Tholey (DE)

(72) Inventors: Lars Thelin, Falun (SE); Fredrik Bokvist, Svärdsjö (SE)

(73) Assignee: URSATEC GMBH, Tholey (DE)

( * ) Notice: Subject to any disclaimer, the term of this patent is extended or adjusted under 35 U.S.C. 154(b) by 0 days.

(21) Appl. No.: 18/718,228

(22) PCT Filed: Nov. 29, 2022

(86) PCT No.: PCT/SE2022/051116
§ 371 (c)(1),
(2) Date: Jun. 10, 2024

(87) PCT Pub. No.: WO2023/106984
PCT Pub. Date: Jun. 15, 2023

(65) Prior Publication Data

US 2025/0073132 A1 Mar. 6, 2025

(30) Foreign Application Priority Data

Dec. 10, 2021 (SE) .................................... 2151518-4

(51) Int. Cl.
*A61J 17/00* (2006.01)
*A61M 11/00* (2006.01)

(52) U.S. Cl.
CPC ............. *A61J 17/001* (2015.05); *A61J 17/10* (2020.05); *A61M 11/003* (2014.02); *A61M 11/007* (2014.02)

(58) Field of Classification Search
CPC .......... A61J 17/001; A61J 17/00; A61J 17/02; A61J 11/02; A61J 17/0053; A61J 17/0005;

(Continued)

(56) References Cited

U.S. PATENT DOCUMENTS 5,904,140 A 5/1999 McGoogan
2009/0062855 A1* 3/2009 Lemery ................ A61M 16/06 128/200.14

(Continued)

FOREIGN PATENT DOCUMENTS

DE 9421156 U1 8/1995
DE 202017006939 11/2018
KR 20210107789 A 9/2021
WO 2018/127464 A1 7/2018

OTHER PUBLICATIONS

International Search Report for International Application No. PCT/SE2022/051116 dated Mar. 1, 2023.

(Continued)

*Primary Examiner* — Majid Jamialahmadi
(74) *Attorney, Agent, or Firm* — Harness, Dickey & Pierce, P.L.C.

(57) ABSTRACT

A pacifier comprising a suction part and a housing part, wherein said suction part comprises a nipple and a shield connected to each other, wherein said suction part comprises a passageway which is passing through the nipple, through which passageway a fluid can pass from outside a mouth of a user of the pacifier to inside the mouth of the user of the pacifier, and wherein said housing part comprises a housing having a drug inlet which is connected or connectable to a drug supplying device, whereby a drug can be fed from the drug supplying device, through the housing of the housing part and then through the passageway of the suction part and into the mouth of the user when the housing part is connected to said suction part, wherein said housing part comprises a drug preparation device configured for transferring the drug received from the drug supplying device to the suction part in a form for inhalation, wherein said drug preparation device comprises an aerosolization device, wherein said housing comprises at least one air inlet and at least one air channel configured for transferring air from said (Continued)

at least one air inlet to the passageway of the suction part, whereby air can be drawn into the housing through said air inlet by a user of the pacifier when the user is inhaling through the passageway of the suction part.

12 Claims, 4 Drawing Sheets

(58) Field of Classification Search
CPC .................. A61J 17/10; A61M 11/003; A61M 15/0021; A61M 15/00
See application file for complete search history.

(56) References Cited

U.S. PATENT DOCUMENTS

| | | | |
|---|---|---|---|
| 2013/0118485 | A1 | 5/2013 | Shahaf |
| 2014/0202457 | A1 | 7/2014 | Addington et al. |
| 2016/0199609 | A1 | 7/2016 | Gulka et al. |
| 2019/0298618 | A1 | 10/2019 | Becker |

OTHER PUBLICATIONS

Extended European search report issued Nov. 6, 2025 in European Application No. 22904769.1.
Examination Report issued Feb. 3, 2026 in Indian Application No. 202417044209.

* cited by examiner

PACIFIER

CROSS-REFERENCE TO RELATED APPLICATIONS

This application is a national phase under 35 U.S.C. § 371 of PCT International Application No. PCT/SE2022/051116 which has an International filing date of Nov. 29, 2022, which claims priority to Swedish Application No. 2151518-4, filed Dec. 10, 2021, the entire contents of each of which are hereby incorporated by reference.

TECHNICAL FIELD

The present invention relates to a pacifier, an exchangeable housing part configured to be used in a pacifier and to a pacifier system.

BACKGROUND

Feeding of drugs to children can often be problematic. The difficulties of providing inhalation drugs to small children are well known and a field of research of its own. The most effective interface for providing adequate doses of inhaled drugs to children is in the form of a mouthpiece. This allows for the least leakage of drugs. Unfortunately, this type of device is not well accepted by most small children. Other means of providing inhalation drugs to children is the face mask, with or without a spacer. This interface is not widely accepted by children and is prone to leakage. In DE9421156 a pacifier for administration of gaseous active substances is disclosed.

There is still a need for more user friendly devices for feeding of inhalation drugs to small children.

SUMMARY

An object of the present invention is to provide an improved device for inhalation of drugs.

A further object of the present invention is to provide an improved pacifier for delivering of drugs.

A further object of the present invention is to provide a more versatile and user friendly pacifier.

This is achieved by a pacifier, an exchangeable housing part and a pacifier system according to the independent claims.

According to one aspect of the invention a pacifier comprising a suction part and a housing part is provided. Said suction part comprises a nipple and a shield connected to each other, wherein said suction part comprises a passageway which is passing through the nipple, through which passageway a fluid can pass from outside a mouth of a user of the pacifier to inside the mouth of the user of the pacifier, and wherein said housing part comprises a housing having an inlet which is connected or connectable to a drug supplying device, whereby a liquid drug can be fed from the drug supplying device, through the housing of the housing part and then through the passageway of the suction part and into the mouth of the user when the housing part is connected to said suction part, wherein said housing part comprises a drug preparation device configured for transferring the liquid drug received from the drug supplying device to the suction part in a form for inhalation, wherein said drug preparation device comprises an aerosolization device, wherein said aerosolization device comprises at least one aerosolization membrane which is a fine pore membrane, whereby said drug will be aerosolized when forced through said at least one aerosolization membrane, wherein said housing comprises at least one air inlet and at least one air channel, said air channel being configured for transferring air from said at least one air inlet to the passageway of the suction part, whereby air can be drawn into the housing through said air inlet by a user of the pacifier when the user is inhaling through the passageway of the suction part.

According to another aspect of the invention an exchangeable housing part configured to be used together with a suction part in a pacifier as described above is provided.

With the pacifier according to the invention inhalation of a drug can be easily performed also to very small children and without any complicated equipment. A liquid drug is fed from the drug supplying device through the drug preparation device and the aerosolization device in the pacifier. The liquid drug will be transferred into a form for inhalation when it is pushed through the aerosolization device. For example, a parent, a nurse or a nanny can assist the user of the pacifier to push the drug from the drug supplying device through the pacifier. The drug supplying device can for example be a syringe comprising the drug and being connected to the pacifier via a tube. The user's own breathing through the pacifier will also improve the administering of the inhalation drug. The pacifier interface is naturally sought after by the child which facilitates the usage. Also, the timing of inhaling the drug is of great importance and can be a significant challenge, especially in non-cooperative patients such as small children. The time required to inhale the drug and the coordination with inhalation are two components which said invention is optimized for. Since the pacifier is comforting for the child the time for inhalation is virtually unlimited, as opposed to other contraptions such as the face mask which may not be tolerated a long time. Furthermore, since inhalation through the pacifier is allowed via the air inlet and air channel the flow of air through the pacifier caused by inhalation will improve drug administration. The air flow from inhalation will be beneficial for transferring the drug to the user. Furthermore, thanks to the nipple protruding a distance into the mouth of the user and the drug will be transferred through the whole nipple before it is released from the nipple, the drug will hereby be administered inside the mouth of the user at a distance from the user's lips corresponding to the length of the nipple. This is advantageous because this optimizes the delivery of drug to the target organ, which can be the upper or lower airways, by bypassing the nasal orifice and a large part of the tongue. With other prior art inhalation devices, the drug is administered outside of the face with a facemask or in proximity to the lips via a mouthpiece. This delivers the dose of drug largely in the nasal orifice, oral mucosa or tongue instead of being delivered to the target organ.

According to another aspect of the invention a pacifier system comprising a reusable suction part and at least two exchangeable housing parts is provided. At least one exchangeable housing is an exchangeable housing as defined above. In some embodiments the pacifier system further comprises at least one exchangeable filter housing part comprising at least one heat and moisture exchanger (HME) device and/or at least one filter device and/or at least one exchangeable drug housing part comprising a drug to be administered to the user.

In some embodiments of the invention the suction part is a reusable part, and the housing part is an exchangeable part, wherein said reusable suction part and said exchangeable housing part are releasable connectable to each other, wherein said suction part comprises at least one first connection device and wherein said housing part comprises at least one second connection device which is releasably connectable to the at least one first connection device. Hereby a versatile pacifier is achieved. The suction part can be reused and connected to different housing parts.

In some embodiments of the invention said passageway comprises a first end and a second end between which a fluid can pass, which first end is provided at a first connection interface of the suction part configured for mating with a second connection interface of the housing part and which second end of the passageway is provided in a part of the nipple which is configured to be positioned within a user's mouth during use of the pacifier, whereby a fluid can pass through the passageway between the first connection interface of the suction part and the inside of a user's mouth during use of the pacifier.

In some embodiments of the invention the housing of the housing part comprises an interior space which is defined by a lid, surrounding walls and the second connection interface which is provided opposite the lid.

In some embodiments of the invention the at least one air channel is provided in the housing separated from the drug preparation device, whereby air inhaled by the user via the at least one air channel and drug supplied via the drug preparation device will be mixed in the passageway of the suction part. Hereby inhalation air can be utilized for helping transferring the drug through the nipple of the pacifier.

In some embodiments of the invention said housing part further comprises a filter device and/or a HME device through which air inhaled by a user of the pacifier is passing. Hereby bacteria and other hazardous substances in the air can be filtered away and inhaled air can be conditioned in a suitable way. The HME, heat and moisture exchanger, device will prevent dehydration of the mouth and throat which causes discomfort. Furthermore, the HME prevents dry, cold air from reaching the lungs. This prevents several negative consequences, e.g. increased work of breathing, stagnation of mucus, lower oxygen levels among others. The use of a filter device inside the housing part of the pacifier will reduce the amount of hazardous substances that a child might otherwise inhale in polluted environments. The type of filter device can be adopted to different environments with varying polluting toxic substances.

In some embodiments of the invention said nipple and said passageway are between 10-37 mm. Hereby the drug will be released inside the mouth of a user of the pacifier relatively far away from the lips of the user. Hereby a less amount of the drug will be lost by not reaching all the way to the target organ.

Further embodiments are described in the dependent claims and in the detailed description.

DETAILED DESCRIPTION OF EMBODIMENTS

Figures 1A, 1B:
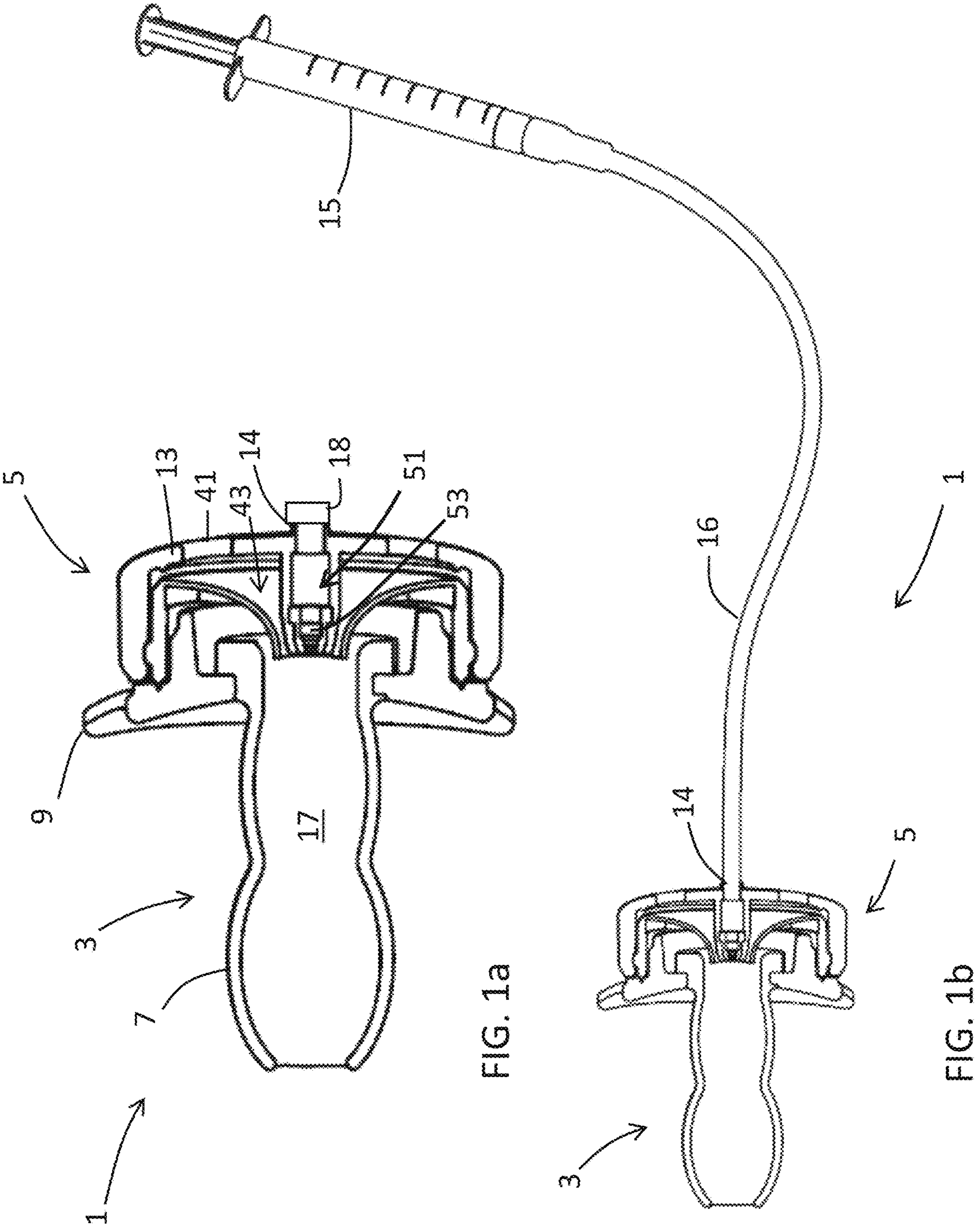
FIGS. 1*a*-1*d* show slightly different examples of a pacifier according to the invention as side view cross sections.
Figure 1C:
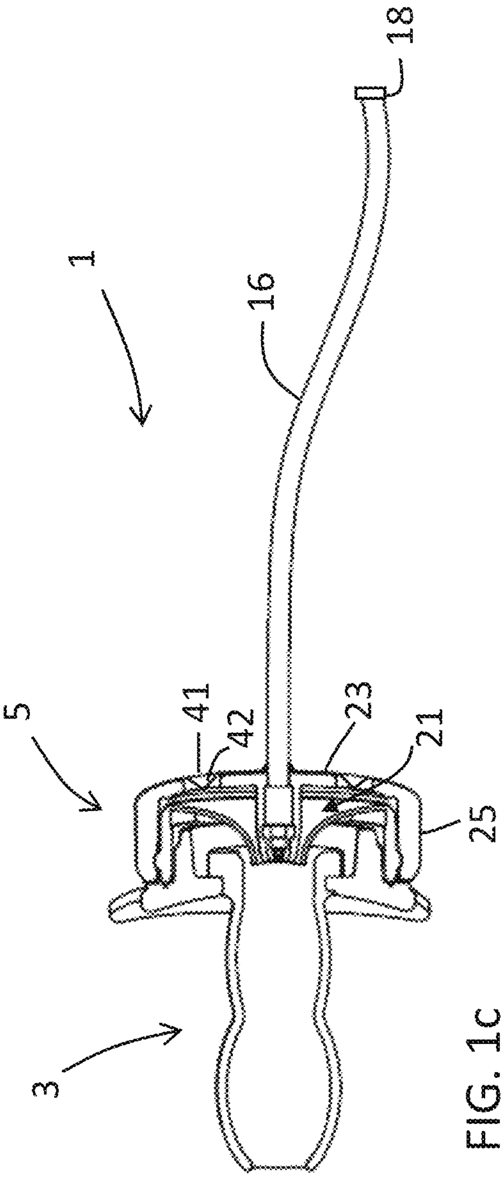
Figure 1D:
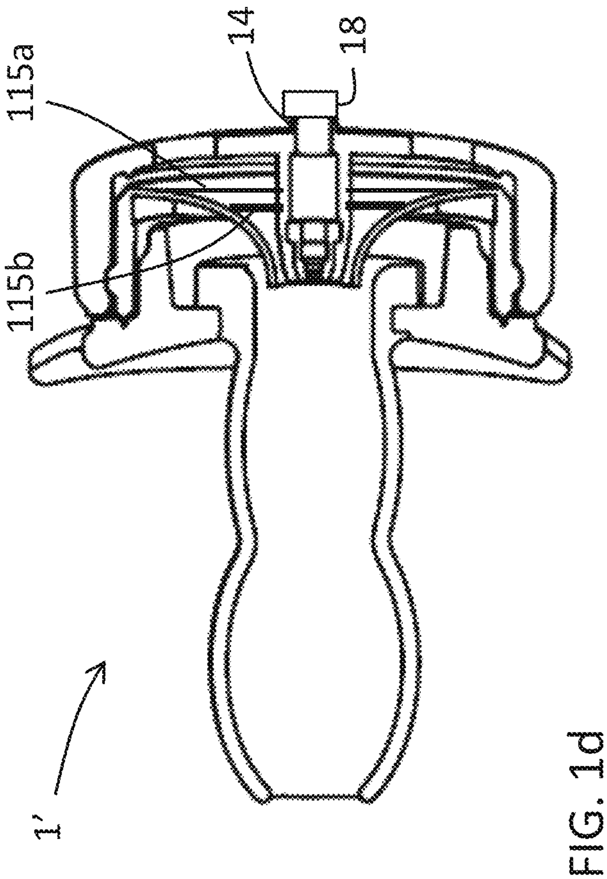

In FIGS. 1*a*-1*d* four different examples of pacifiers 1; 1' according to the invention are shown. Most of the details are the same in these different examples and are also given the same reference numbers. The pacifier 1; 1' according to the invention may either comprise a drug supplying device 15 (as shown in FIG. 1*b*) or may be configured for being possible to connect to a drug supplying device 15, for example via a tube 16. The drug supplying device 15 could be for example a syringe into which a liquid drug to be used for inhalation can be provided. The pacifier 1 could in some examples only comprise a drug inlet 14 which is configured for being connectable to a drug supplying device 15, i.e. the pacifier does not in these examples comprise the drug supplying device 15 or a tube 16 for connection to the drug supplying device. This is shown in FIG. 1*a*. In other examples the pacifier 1 may comprise both the tube 16 and the drug supplying device 15 (as shown in FIG. 1*b*) or only the tube 16 for connection to a separately provided drug supplying device 15 (as shown in FIG. 1*c*). In FIG. 1*d* a pacifier 1' according to one example of the invention is shown, which pacifier further comprises a filter 115*a* and/or a HME (heat and moisture exchanger) device 115*b* which will be further described below.

Figures 2A, 2B, 2C:
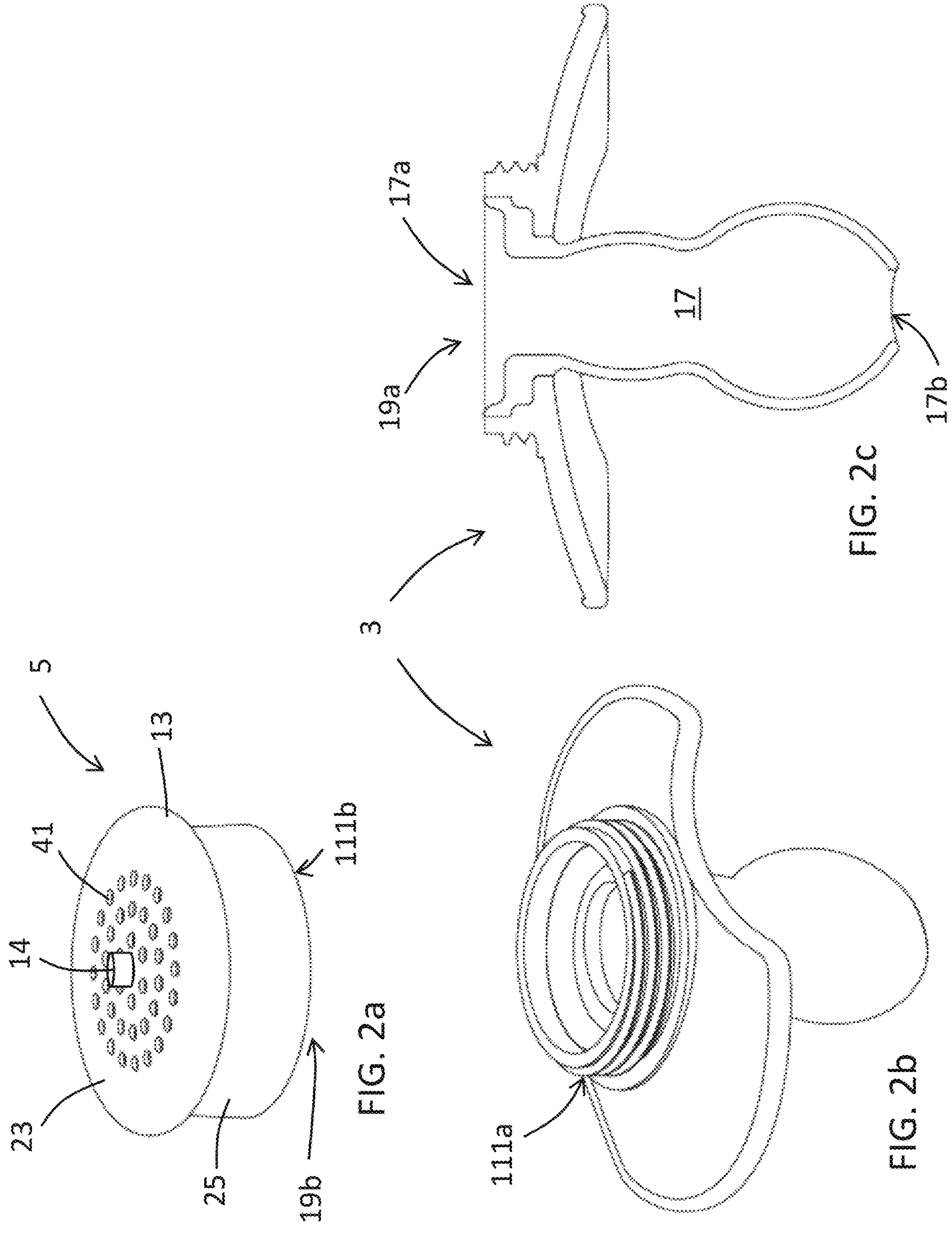
FIG. 2*a* shows schematically a housing part according to some examples of the invention.
FIG. 2*b* shows schematically a suction part according to some examples of the invention.
FIG. 2*c* is a side view cross section of the suction part as shown in FIG. 2*b*.

In all the examples as shown in FIGS. 1*a*-1*d*, the drug is a liquid drug for inhalation and the pacifier 1; 1' comprises an aerosolization device 53 for transforming the liquid drug into a form for inhalation. In FIG. 2*a* a housing part 5 according to some examples of the invention is shown separate from the suction part 3 and in FIG. 2*b* a suction part 3 is shown separate from the housing part 5. FIG. 2*c* is a cross section of the suction part 3 as shown in FIG. 2*b*. The pacifier 1; 1' according to the invention will be described with reference to all the drawings 1*a*-1*d* and 2*a*-2*c*.

According to the invention a pacifier 1; 1' comprising a suction part 3 and a housing part 5 is provided. The suction part 3 comprises a nipple 7 and a shield 9 connected to each other. The suction part 3 comprises further a passageway 17 which is passing through the nipple, through which passageway 17 a fluid can pass from outside a mouth of a user of the pacifier to inside the mouth of the user of the pacifier. The housing part 5 comprises a housing 13 having a drug inlet 14 which is connected or connectable to a drug supplying device 15, possibly via a tube 16 as shown in FIGS. 1*b* and 1*c*. The drug inlet 14 is configured for being connected to a drug supplying device 15. Hereby, when said pacifier is connected to a drug supplying device 15, a liquid drug can be fed from the drug supplying device 15, through the housing 13 of the housing part 5 and then through the passageway 17 of the suction part 3 and into the mouth of the user when the housing part 5 is connected to said suction part 3. The pacifier is adapted for transferring a drug to be inhaled. Hereby the user is inhaling the drug after it has been passing through the passageway 17 of the suction part 3. The housing part 5 comprises a drug preparation device 51 configured for transferring the liquid drug received from the drug supplying device 15 to the suction part 3 in a form for inhalation, wherein said drug preparation device 51 comprises an aerosolization device 53. Hereby the drug is provided from the drug supplying device 15 in a liquid form and the drug will be aerosolized into a form suitable for inhalation when passing the aerosolization device 53 of the drug preparation device 51. Said housing 13 comprises furthermore at least one air inlet 41 and at least one air channel 43. The at least one air channel 43 is configured for transferring air from said at least one air inlet 41 to the passageway 17 of the suction part 3. Hereby air can be drawn into the housing 13 through said air inlet 41 by a user of the pacifier 1; 1' when the user is inhaling through the passageway 17 of the suction part 3. Hereby drug and inhalation air will be mixed in the passageway 17 passing through the nipple 7. The flow of inhalation air will help to forward the drug further into the mouth of the user of the pacifier. The drug will hereby be administered in a position within the mouth of the user, which position is determined by a length of the nipple. The length of said nipple 7 is in some examples between 10-37 mm. Hereby the drug will be administered comparatively deep into the mouth of the user and closer to the throat of the user compared to conventional inhalation devices which only deliver the drug right beneath the lips or in front of the mouth. This is advantageous because less drug will escape out into the surrounding room according to the invention and less drug will stick to surfaces in the mouth and nose compared to conventional inhalation devices.

Furthermore, a design and size of the at least one air inlet 41 and the at least one air channel 43 can be optimized such that a suitable resistance to airflow through the pacifier is achieved. Hereby, breathing may partly also be performed via the nose which may be suitable for drug transportation into trachea. Hereby delivery of medication to the target organ can be optimized.

In some embodiments of the invention the suction part 3 is a reusable part and the housing part 5 is an exchangeable part, wherein said reusable suction part 3 and said exchangeable housing part 5 are releasably connectable to each other. This is shown in FIGS. 2*a*, 2*b* and 2*c*. The suction part 3 comprises in these embodiments at least one first connection device 111*a* and the housing part 5 comprises at least one second connection device 111*b* which is releasably connectable to the at least one first connection device 111*a*. All the embodiments as shown in FIGS. 1*a*-1*d* can be provided either as one single part where the suction part 3 and the housing part 5 are fixedly connected to each other or as two releasably connected parts, where the suction part 3 and the housing part 5 are releasably connected to each other.

With reference to FIGS. 2*a* and 2*c* some further details of the pacifier are now described. The passageway 17 comprises a first end 17*a* and a second end 17*b* between which a fluid can pass, which first end 17*a* is provided at a first connection interface 19*a* of the suction part 3 configured for mating with a second connection interface 19*b* of the housing part 5 for embodiments where the suction part and the housing part are releasably connected. For embodiments where the housing part 5 and the suction part 3 are fixedly connected the first and second connection interfaces 19*a*, 19*b* are of course already mated. The second end 17*b* of the passageway 17 is provided in a part of the nipple 7 which is configured to be positioned within a user's mouth during use of the pacifier 1; 1', whereby a fluid can pass through the passageway 17 between the first connection interface 19*a* of the suction part 3 and the inside of a user's mouth during use of the pacifier.

Furthermore, the housing 13 of the housing part 5 comprises an interior space 21 (pointed to in FIG. 1*c*) which is defined by a lid 23, surrounding walls 25 and the second connection interface 19*b* which is provided opposite the lid 23. The lid 23 comprises the at least one air inlet 41.

The aerosolization device 53 comprises in some examples at least one aerosolization membrane which is a fine pore membrane, whereby said drug will be aerosolized when forced through said at least one aerosolization membrane. Pressure is applied by a user from the drug supply device 15 for forcing the drug through the aerosolization membrane. In the case where the drug supplying device is a syringe, pressure is applied by pressing a plunger of the syringe further into the syringe for transferring the drug via the tube 16 to the pacifier 1; 1'. The sizes of the pores in the aerosolization membrane and the thickness of the membrane will decide the size of the aerosol droplets which are then inhaled, this size is important for where the droplets are then deposited in the respiratory tract.

The aerosolization membrane can be positioned at any position in the housing part 5. It may be positioned close to the lid 23 or further away from the lid 23 and closer to the suction part 3. It may even be provided protruding into the passageway 17 in the nipple 7.

A closing member 18 can be provided to the drug inlet 14. This is shown in FIGS. 1*a* and 1*d* and such a closing member 18 can be removed before connection to a drug supplying device 15. In FIG. 1*c* the closing device 18 is instead provided at the end of a tube 16 which is provided connected to the pacifier 1.

Said at least one air inlet 41 is in some embodiments provided with one or more valves 42 such that passage of air via said at least one air inlet 41 only is admitted towards the mouth and not outwards from said housing 13. Such a valve 42 is an optional feature and is only shown in FIG. 1*c* but can be provided in all embodiments of the invention. This may be suitable in order to avoid any leakage of drug out from the housing while exhaling.

The material of the nipple is a flexible, plastic material which can be coated with active surface materials such as electrostatic inhibitors or anti-bacterial coating.

The first and second connection device 111*a*, 111*b* of the suction part 3 and the housing part 5 can be threaded connection devices 111*a*, 111*b* as shown in FIGS. 2*a*, 2*b* and 2*c*. However, other connection devices 111*a*, 111*b* are of course possible. For example, a snap connection with or without rotation locking of the housing part to the suction part could be provided. A snap connection where either the first or the second connection device 111*a*, 111*b* comprises protruding parts and the other comprises recesses into which the protruding parts can be received is also possible. Other connection devices comprising for example a rotation lock mechanism is also possible. In another example the first connection device 111*a* comprises two opposing recesses and the second connection device 111*b* comprises two protruding parts, whereby the recesses are configured to receive the protruding parts when the suction part 3 and the housing part 5 are connected. For allowing the protruding parts to enter the recesses the protruding parts may be resilient. Another alternative is that for example the shield 9 is resilient and can be bent to allow the protruding parts to enter into the recesses. The number of recesses and protruding parts can of course be another than two. Furthermore, the recesses could as well be provided in the housing part 5 and the protruding parts in the suction part 3. For improving the connection and securing the connection, a rotational locking feature can as well be provided. By rotating the housing part 5 in relation to the suction part 3 when they have been connected the first and second connection devices 111*a*, 111*b* can be provided in a locking position. For example, the recesses can be provided as grooves allowing protruding parts to be guided in the grooves when the housing part is rotated.

Figure 3:
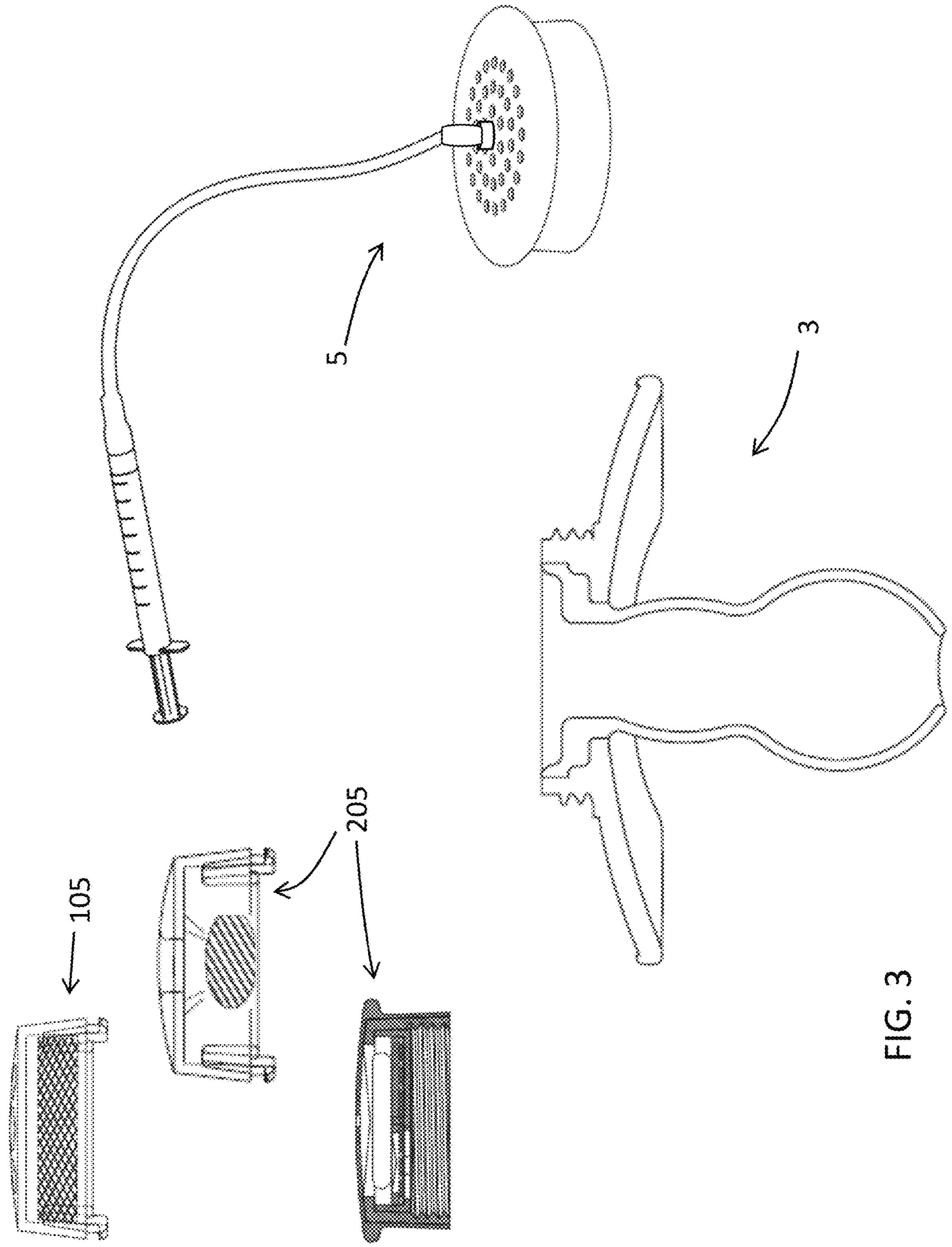
FIG. 3 shows a pacifier system according to a few examples of the invention.

One alternative connection device is shown in FIG. 3, where a filter housing part 105 and a drug housing part 205 comprising a snap connection device are shown. However, the suction part 3 as shown in FIG. 3 will not fit these housing parts but would need a corresponding snap connection device.

In any of the pacifier 1; 1' examples as described above in relation to FIGS. 1*a*-2*c* a filter and/or a HME device could also be provided. This is schematically shown in FIG. 1*d* where a filter 115*a* and a HME device 115*b* are schematically illustrated to be inserted into the housing part 5 of the pacifier 1'. Hereby air inhaled via the pacifier will pass the filter 115*a* and the HME device 115*b* and the air will be filtered and conditioned. Bacteria or other hazardous substances such as toxic substances can be filtered away before being inhaled and the HME, heat and moisture exchanger, device will prevent dehydration of the mouth and throat which causes discomfort. Furthermore, the HME prevents dry, cold air from reaching the lungs. Only one of the filter or HME device can as well be provided in the pacifier 1; 1'.

According to another aspect of the invention an exchangeable housing part 5 configured to be used in a pacifier as described above is provided. The housing part 5 is designed as already described above. The housing part 5 comprises a housing 13 and at least one second connection device 111*b* which is releasably connectable to at least one first connection device 111*a* provided in the suction part 3, wherein said housing 13 comprises a drug inlet 14 which is connected or connectable to a drug supplying device 15, possibly via a tube 16 as shown in FIGS. 1*b* and 1*c*. The housing part 5 comprises a drug preparation device 51 configured for transferring the drug received from the drug supplying device 15 to the suction part 3 in a form for inhalation, wherein said drug preparation device 51 comprises an aerosolization device 53. Said housing 13 comprises furthermore at least one air inlet 41 and at least one air channel 43 configured for transferring air from said at least one air inlet 41 to the passageway 17 of the suction part 3. All the details described above with reference to the FIGS. 1-2 are also applicable to the exchangeable housing part 5 according to the invention and will not be described again.

A pacifier system can also be provided comprising one suction part 3 and more than one housing parts 5 which are intended for use with the same suction part 3. Hereby the suction part 3 can be reused together with different housing parts 5. The pacifier 1; 1' can be delivered as a kit with one suction part 3 and a number of housing parts 5.

A pacifier system is illustrated in FIG. 3. The pacifier system comprises a reusable suction part 3 and at least two exchangeable housing parts 5. At least one of the housing parts 5 can be a housing part as described above in relation to FIGS. 1 and 2. In the pacifier system other types of housing parts 105; 205 may also be provided, such as a drug housing part 205 comprising a drug to be provided via the suction part 3 to the user of the pacifier and/or a filter housing part 105 comprising a filter and/or a HME device as discussed above. More than one of these different examples can also be provided in combination in a housing part. For example, an exchangeable housing part may comprise both a drug and a filter. By providing a pacifier system one suction part can be used for different types of housing parts and a suitable housing part can be provided for different occasions. Furthermore, new housing parts can be provided when the first one is empty of drug or when a filter needs to be changed. Hereby a user friendly and environmentally friendly product which is flexible for different needs is achieved.

The invention claimed is:

1. A pacifier comprising a suction part and a housing part, wherein said suction part comprises a nipple and a shield connected to each other, wherein said suction part comprises a passageway which is passing through the nipple, through which said passageway a fluid can pass from outside a mouth of a user of the pacifier to inside the mouth of the user of the pacifier, and wherein said housing part comprises a housing having a drug inlet which is connected or connectable to a drug supplying device, whereby a liquid drug can be fed from the drug supplying device, through the housing of the housing part and then through the passageway of the suction part and into the mouth of the user when the housing part is connected to said suction part, wherein said housing part comprises a drug preparation device configured for transferring the liquid drug received from the drug supplying device to the suction part in a form for inhalation, wherein said drug preparation device comprises an aerosolization device, wherein said housing comprises at least one air inlet and at least one air channel, said at least one air channel being configured for transferring air from said at least one air inlet to the passageway of the suction part, whereby air can be drawn into the housing through said at least one air inlet by a user of the pacifier when the user is inhaling through the passageway of the suction part, wherein the suction part is a reusable part and the housing part is an exchangeable part, wherein said reusable suction part and said exchangeable housing part are releasable connectable to each other, wherein said suction part comprises at least one first connection device and wherein said housing part comprises at least one second connection device which is releasably connectable to the at least one first connection device.

2. The pacifier according to claim 1, wherein said passageway comprises a first end and a second end between which a fluid can pass, which first end is provided at a first connection interface of the suction part configured for mating with a second connection interface of the housing part and which second end of the passageway is provided in a part of the nipple which is configured to be positioned within the user's mouth during use of the pacifier, whereby a fluid can pass through the passageway between the first connection interface of the suction part and the inside of the user's mouth during use of the pacifier.

3. The pacifier according to claim 2, wherein the housing of the housing part comprises an interior space which is defined by a lid, surrounding walls and the second connection interface which is provided opposite the lid.

4. The pacifier according to claim 1, wherein the at least one air channel is provided in the housing separated from the drug preparation device, whereby air inhaled by the user via the at least one air channel and drug supplied via the drug preparation device will be mixed in the passageway of the suction part.

5. The pacifier according to claim 1, wherein said housing part further comprises a filter device and/or a HME device through which air inhaled by a user of the pacifier is passing.

6. The pacifier according to claim 1, wherein a length of said nipple and said passageway is between 10-37 mm.

7. The pacifier according to claim 1, wherein said aerosolization device comprises at least one aerosolization membrane, which is a fine pore membrane, whereby said drug will be aerosolized when forced through said at least one aerosolization membrane.

8. The pacifier according to claim 1, wherein the user's breathing through the pacifier provides a flow in the air from the at least one air inlet to the passageway to administer the drug into the user's mouth.

9. An exchangeable housing part configured to be used together with the suction part in the pacifier according to claim 1, wherein said exchangeable housing part comprises a housing having a drug inlet which is connected or connectable to a drug supplying device, whereby a liquid drug can be fed from the drug supplying device, through the housing of the exchangeable housing part and then through the passageway of the suction part and into the mouth of the user when the exchangeable housing part is connected to said suction part, wherein said exchangeable housing part comprises a drug preparation device configured for transferring the liquid drug received from the drug supplying device to the suction part in a form for inhalation, wherein said drug preparation device comprises an aerosolization device, wherein said housing comprises at least one air inlet and at least one air channel configured for transferring air from said at least one air inlet to the passageway of the suction part, whereby air can be drawn into the housing through said at least one air inlet by a user of the pacifier when the user is inhaling through the passageway of the suction part, wherein the suction part is a reusable part, wherein said reusable suction part and said exchangeable housing part are releasable connectable to each other, wherein said suction part comprises at least one first connection device and wherein said housing part comprises at least one second connection device which is releasably connectable to the at least one first connection device.

10. The exchangeable housing part according to claim 9, wherein said aerosolization device comprises at least one aerosolization membrane, which is a fine pore membrane, whereby said drug will be aerosolized when forced through said at least one aerosolization membrane.

11. A pacifier system comprising a pacifier including a housing part wherein the housing part is the exchangeable housing part according to claim 9 and wherein the pacifier system comprises at least two exchangeable housing parts.

12. A pacifier system comprising a pacifier including a housing part, wherein the housing part is the exchangeable housing part according to claim 9 and wherein the pacifier system further comprises at least one exchangeable filter housing part comprising at least one heat and moisture exchanger (HME) device and/or at least one filter device and/or at least one exchangeable drug housing part.

* * * * *